United States Patent
Isaacson et al.

(10) Patent No.: US 10,744,299 B2
(45) Date of Patent: Aug. 18, 2020

(54) OBTURATOR ASSEMBLY WITH SELECTIVELY CONTROLLABLE FLUID FLOW PATH

(71) Applicant: Becton, Dickinson and Company, Franklin Lakes, NJ (US)

(72) Inventors: S. Ray Isaacson, Layton, UT (US); Mark Hunter, Herriman, UT (US); Paul Walker, Sandy, UT (US); Jeff O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 239 days.

(21) Appl. No.: 15/697,140

(22) Filed: Sep. 6, 2017

(65) Prior Publication Data

US 2019/0069973 A1 Mar. 7, 2019

(51) Int. Cl.
*A61M 25/00* (2006.01)
*A61C 5/50* (2017.01)
*A61C 5/40* (2017.01)

(52) U.S. Cl.
CPC .......... *A61M 25/0074* (2013.01); *A61C 5/40* (2017.02); *A61C 5/50* (2017.02); *A61M 2025/0004* (2013.01); *A61M 2025/0006* (2013.01); *A61M 2025/0019* (2013.01); *A61M 2025/0079* (2013.01)

(58) Field of Classification Search
CPC ............ A61M 25/0074; A61M 25/007; A61M 25/0067; A61M 2025/0018; A61M 2025/0079; A61M 5/344–346; A61M 5/348
See application file for complete search history.

(56) References Cited

U.S. PATENT DOCUMENTS

| 4,180,068 A | 12/1979 | Hansen et al. | |
|---|---|---|---|
| 5,201,712 A * | 4/1993 | Bryant | A61M 25/00 604/164.02 |
| 2007/0016124 A1* | 1/2007 | McGraw | A61M 25/003 604/4.01 |
| 2009/0018529 A1* | 1/2009 | Hoffman | A61F 2/95 604/529 |
| 2010/0069855 A1* | 3/2010 | Ross | A61F 2/95 604/529 |
| 2012/0323175 A1* | 12/2012 | Vogelbaum | A61M 25/0054 604/95.04 |
| 2013/0204208 A1 | 8/2013 | Olson et al. | |

FOREIGN PATENT DOCUMENTS

WO 2005/023336 3/2005

* cited by examiner

*Primary Examiner* — Rebecca E Eisenberg
*Assistant Examiner* — Tasnim Mehjabin Ahmed
(74) *Attorney, Agent, or Firm* — Kirton McConkie; Craig Metcalf; Kevin Stinger (57) ABSTRACT

An obturator assembly includes an obturator positionable within a lumen of a device and movable within the lumen between a first position and a second position. The obturator includes a distal tip portion, wherein, with the obturator in the first position, the distal tip portion limits fluid communication through the lumen and, with the obturator in the second position, the distal tip portion provides fluid communication through the lumen.

17 Claims, 7 Drawing Sheets

OBTURATOR ASSEMBLY WITH SELECTIVELY CONTROLLABLE FLUID FLOW PATH

TECHNICAL FIELD

The present application relates generally to an obturator assembly. More specifically, the present application relates to an obturator assembly having an obturator movably positioned within a catheter to selectively control a fluid flow through the catheter.

BACKGROUND

Commonly, conventional IV catheters are keep clear of clotting occlusions during their useful life by flushing the IV catheter periodically with saline or another suitable cleansing fluid or liquid. During the flushing process, the fluid is moved through the catheter to flush out any thrombus-forming clotting material contained within the catheter. Alternatively, some conventional IV catheters are keep clear of clotting occlusions by using an obturator to physically occupy a space within the IV catheter lumen. The obturator method is not universally accepted because it requires the doctor or nurse to place the obturator, which may have been recently exposed to an unsterile external environment, into the lumen of the catheter. This method may increase a risk of infection to the patient by positioning the obturator directly into the catheter such that the obturator may contact the patient's blood stream. Further, when the IV catheter is used in a therapy setting, the obturator must be removed and discard, and a replacement obturator is required.

Many conventional obturators are positioned with in the catheter in order to provide the occlusion prevention, and then removed to provide fluid aspiration and/or infusion therapy. The used obturator should be discarded after each use. This process must be repeated every time the IV catheter is accessed.

BRIEF SUMMARY OF SOME EXAMPLE EMBODIMENTS

In one aspect, an obturator assembly, includes a hub forming a central passage. A catheter has a distal end and an opposing proximal end. The catheter includes a small-bore connector at the proximal end coupled to the hub. The catheter forms a lumen extending between the distal end and the proximal end of the catheter. The lumen is in fluid communication with the central passage. An obturator is movably positioned within the lumen. The obturator is movable between a first position and a second position. The obturator includes a distal end having a tip portion. With the obturator in the first position, the distal end limits fluid flow through the lumen and, with the obturator in the second position, the distal end provides a fluid flow path through the lumen.

In another aspect, an obturator is positionable within a lumen of a device and movable within the lumen between a first position and a second position. The obturator includes a distal tip portion. With the obturator in the first position, the distal tip portion limits fluid communication through the lumen of the device and, with the obturator in the second position, the distal tip portion provides fluid communication through the lumen of the device.

In yet another aspect, a method for selectably controlling a fluid flow in an obturator assembly is provided. The obturator assembly includes an obturator positioned within a lumen of a device, such as a catheter. The obturator is movable within the lumen between a first position and a second position. The method includes urging a proximal end of the obturator to move the obturator in a first direction within the lumen in one of a distal direction or a proximal direction with respect to a distal end of the catheter to provide a fluid flow path through the lumen.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Reference herein to any industry standards (e.g., ASTM, ANSI, IEEE, ISO standards) is defined as complying with the currently published standards as of the original filing date of this disclosure concerning the units, measurements, and testing criteria communicated by those standards unless expressly otherwise defined herein. The terms "proximal" and "distal" are used herein in the common usage sense where they refer respectively to a handle/doctor-end of a device or related object and a tool/patient-end of a device or related object. The terms "about," "substantially," "generally," and other terms of degree, when used with reference to any volume, dimension, proportion, or other quantitative or qualitative value, are intended to communicate a definite and identifiable value within the standard parameters that would be understood by one of skill in the art (equivalent to a medical device engineer with experience in this field), and should be interpreted to include at least any legal equivalents, minor but functionally-insignificant variants, standard manufacturing tolerances, and including at least mathematically significant figures (although not required to be as broad as the largest range thereof).

With reference to FIGS. 1-12, in example embodiments, an obturator assembly includes a catheter having a distal end and an opposing proximal end. The catheter forms a lumen extending between the distal end and the proximal end of the catheter. An obturator is movably positioned within the lumen between a first position and a second position. The obturator includes a distal tip portion. With the obturator in the first position, the distal tip portion prevents or limits fluid communication and/or fluid flow through the lumen. Conversely, with the obturator in the second position, the distal tip portion provides fluid communication and/or fluid flow through the lumen. The obturator can be locked or secured in the first position or the second position. The obturator is movable in at least one of a distal direction with respect to the distal end of the catheter or a proximal direction with respect to the distal end of the catheter from the first position to the second position. A hub forms a central passage that is in fluid communication with the lumen with the hub coupled to the catheter. A collar is operatively coupled to the hub and is configured in a locked configuration to prevent movement of the obturator within the lumen and in an unlocked configuration to allow movement of the obturator within the lumen. In the locked configuration, the collar is configured to prevent movement of the obturator within the lumen with the obturator in the first position or the second position. The collar may be biased toward the locked configuration with the obturator in the first position or the second position. In example embodiments, at least a portion of the distal end of the obturator, e.g., at least a portion of a tip portion, has a symmetrical profile with respect to a central axis of the obturator or an asymmetrical profile with respect to the central axis.

The example embodiments described herein provide an obturator to prevent catheter occlusion that is not required to be removed prior to therapy. Rather, the multiple state obturator can be positioned in several states. For example, in a first or closed state, the obturator is configured to close or block a lumen of the catheter to prevent occlusion and/or undesirable reverse blood flow, for example. In a second state, the obturator can be moved within the lumen in a distal direction and/or an opposite proximal direction. Further, the obturator may have a reduced outer diameter in certain embodiments such that when the obturator is advanced, the obturator provides a fluid flow path or fluid opening to allow blood return or fluid infusion. As a result, the obturator does not have to be removed from the catheter lumen; thus, reducing a risk for infection and providing a reliable occlusion prevention mechanism. In particular embodiments, the obturator is made of a suitable translucent material to act as a conduit for light-based disinfectant technology used in reducing bioburden in the intraluminal space, for example. As described herein, the example multiple state obturator is selectively controllable to prevent or allow fluid flow through the catheter without having to be removed. The obturator assembly can remain installed for the duration of the therapy and provide both an anti-occlusion mechanism and an infusion capability.

In example embodiments, an obturator assembly includes an obturator positionable within a lumen of a device, such as a catheter. The obturator is movable between a first position and a second position. The obturator has a distal tip portion, wherein, with the obturator in the first position, the distal tip portion limits fluid communication through the lumen of the device and, with the obturator in the second position, the distal tip portion provides or allows fluid communication through the lumen of the device. The obturator is configured to move automatically in a distal direction with respect to a device, e.g., the catheter, toward a second or open position in response to a pressure causing fluid to flow through the catheter lumen in the distal direction to allow the fluid to be expressed from the distal opening of the lumen. With the pressure decreased or removed, the obturator is configured to move automatically toward a first or closed position. For example, a suitable pump operatively coupled to the obturator assembly may cycle to push fluid into the proximal end of the obturator assembly. In certain embodiments, the obturator includes a spring or another suitable biasing member biasing the spring obturator toward the closed position. The obturator is configured to automatically extend from the device, e.g., the catheter, in a distal direction to allow the fluid to exit the catheter lumen at the opposing distal end of the obturator assembly. Once the fluid has passed through the lumen and the fluid pressure within the lumen is decreased, e.g., removed, the obturator is configured to move automatically toward the first or closed position to seal the distal opening of the catheter. In particular embodiments, the pump may be configured to pump some fluid then reverse its peristaltic condition when used with a movable obturator to more fully re-seat the obturator in the sealed position.

Figure 1:
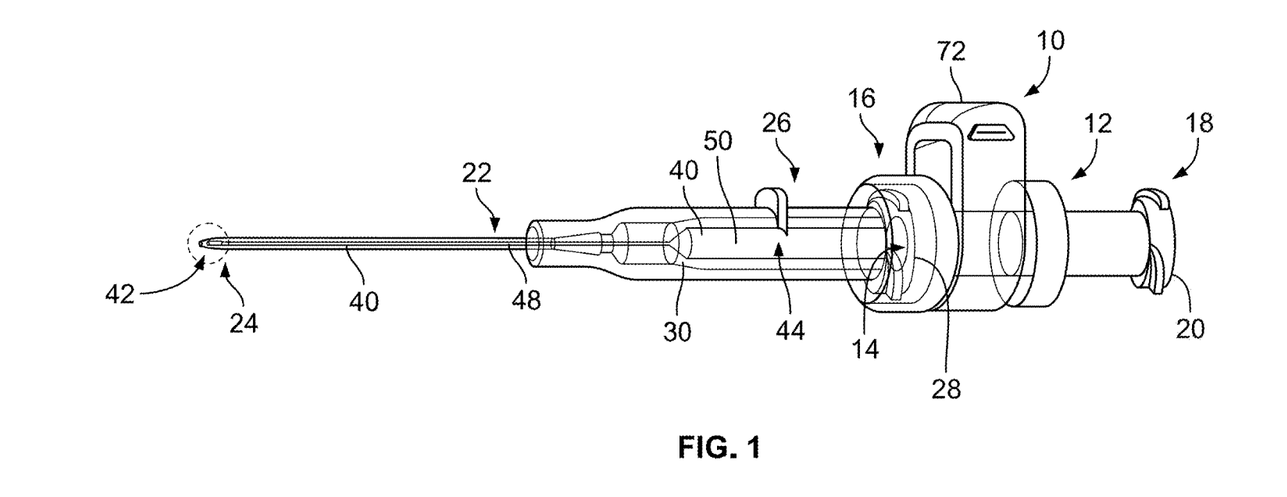
FIG. 1 is a perspective side view of an example obturator assembly in a closed fluid flow path configuration according to example embodiments.
Figure 2:
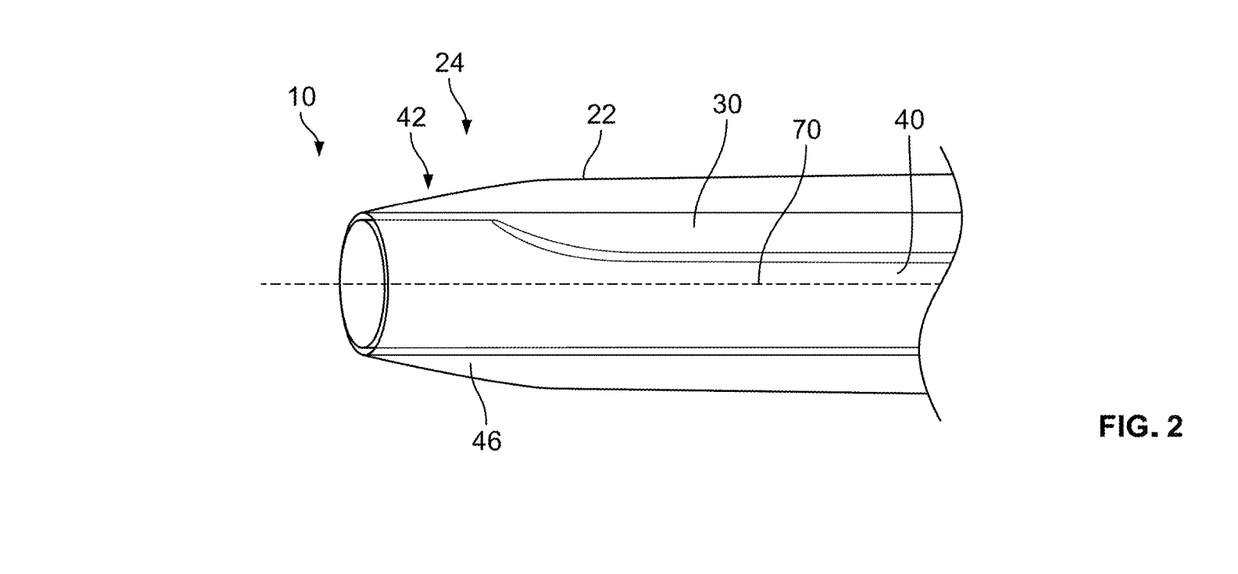
FIG. 2 is a partial perspective side view of the example obturator assembly shown in FIG. 1.
Figure 3:
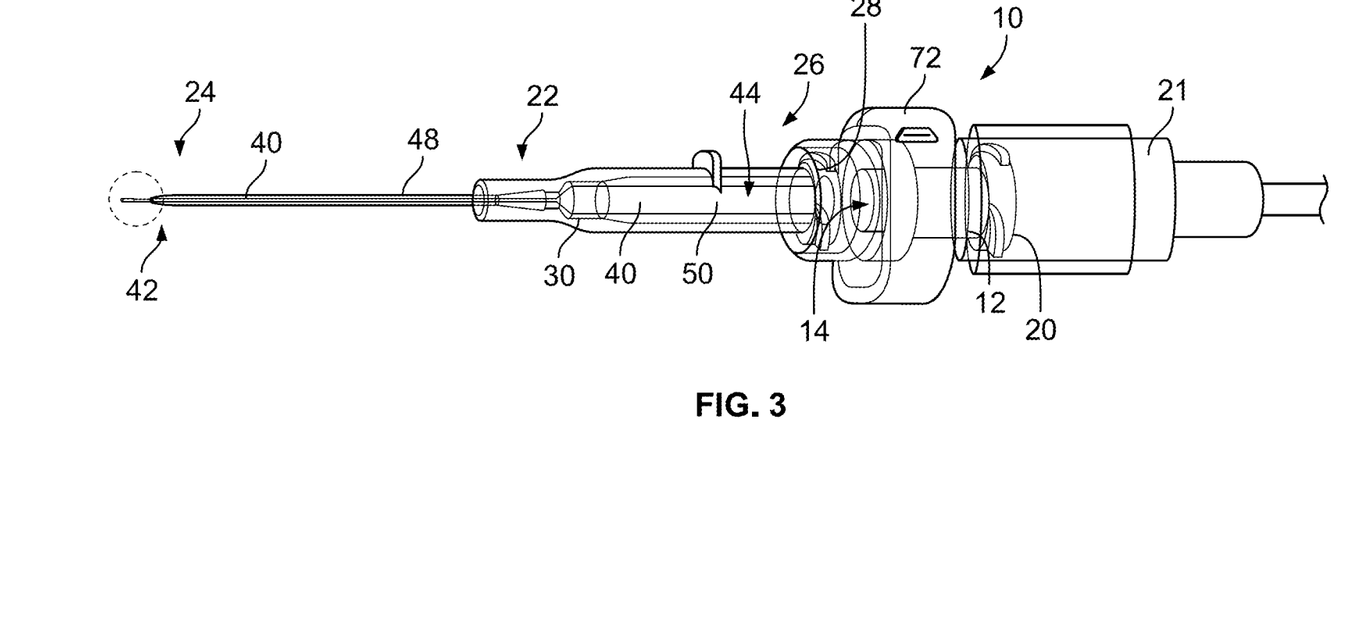
FIG. 3 is a perspective side view of an example obturator assembly in an open fluid flow path configuration according to example embodiments.

Referring now to the figures, and initially to FIGS. 1-5, an example obturator assembly 10 includes a hub 12 forming a central passage 14 as shown in FIGS. 1 and 3. In example embodiments, central passage 14 extends between a distal end 16 and an opposing proximal end 18 of hub 12. As used herein, the terms "distal" and "distally" refer to a location, a position, and/or a direction situated away from the hub, i.e., a point of origin or attachment, while the terms "proximal" and "proximally" refer to a location, a position and/or a direction situated toward the hub, i.e., the point of origin or attachment. Proximal end 18 of hub 12 is configured to removably couple to any suitable medical device or component, for example, standard medical tubing. As shown in FIGS. 1 and 3, for example, a suitable adapter 20 is formed on or coupled to proximal end 18 to facilitate coupling hub 12 to the medical device or tubing. In certain embodiments, hub 12 includes a small-bore connector configured to couple hub 12 to a medical device or tubing. The medical device or tubing may include a cooperating element 21 shown in FIG.

3, such as a small-bore connector lock, to facilitate coupling the medical device or tubing, for example, to hub 12.

A catheter 22 is operatively coupled to hub 12. In example embodiments, catheter 22 has a distal end 24 and an opposing proximal end 26. Catheter 22 may include a cannula extending from a distal end 24 toward an opposing proximal end 26 of catheter 22 in certain example embodiments. At proximal end 26, catheter 22 includes an adapter or body, such as a small-bore connector 28 shown in FIGS. 1 and 3, for example, to couple proximal end 26 of catheter 22 to distal end 16 of hub 12. In certain embodiments, small-bore connector 28 is a small-bore connector having a 6% tapered fluid connection per ISO 80369 for liquids and gases in healthcare applications. In example embodiments, catheter 22 forms or defines a lumen 30 extending between distal end 24 and proximal end 26 of catheter 22. In example embodiments shown in FIGS. 1 and 3, lumen 30 is in fluid communication with central passage 14 to provide a fluid flow path through obturator assembly 10. In example embodiments, each of lumen 30 and central passage 14 has a suitable diameter or a suitable cross-sectional dimension to facilitate fluid flow through obturator assembly 10. More specifically, in certain embodiments, fluid flows around a distal end of an obturator, such as an obturator 40 described below, movably positioned in lumen 30 and into and through lumen 30 of catheter 22 with the obturator in an open position or configuration.

Figure 6:
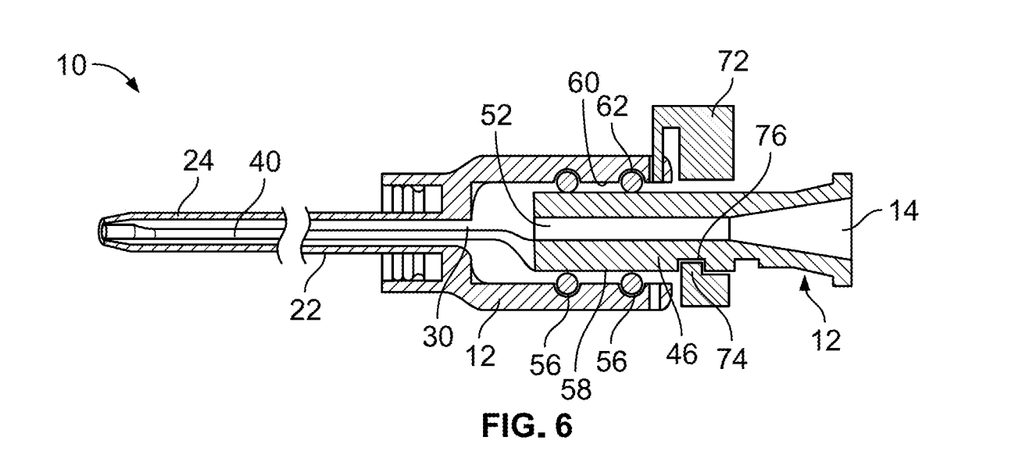
FIG. 6 is a schematic side view of an example obturator assembly in a locked closed fluid flow path configuration according to example embodiments.
Figure 7:
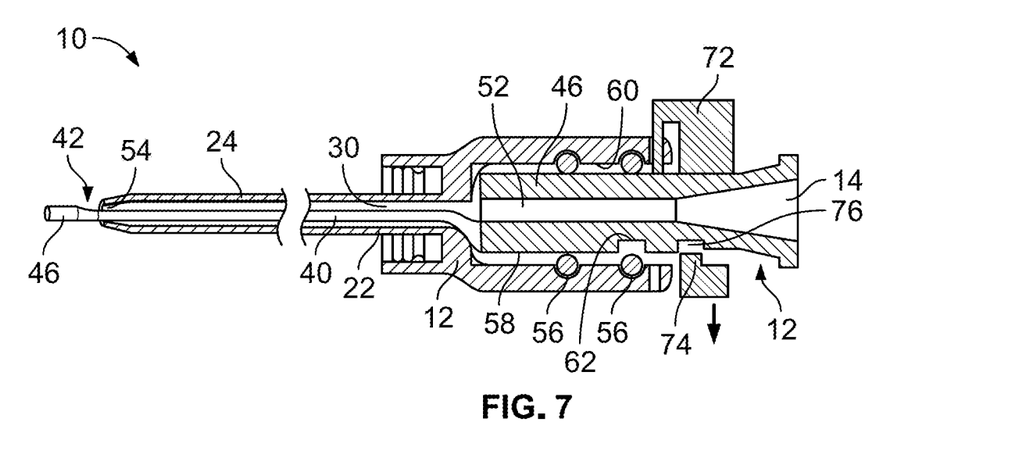
FIG. 7 is a schematic side view of an example obturator assembly in an unlocked open fluid flow path configuration according to example embodiments.
Figure 8:
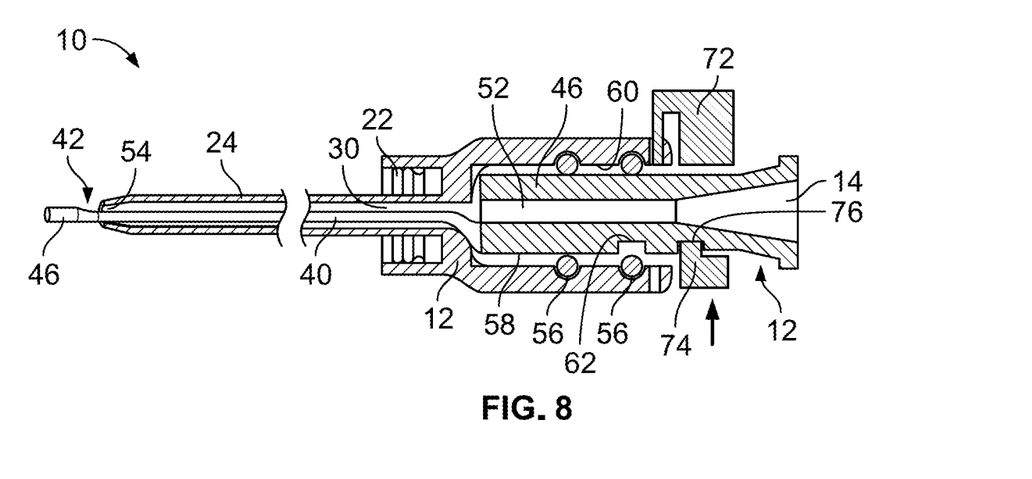
FIG. 8 is a schematic side view of an example obturator assembly in a locked open fluid flow path configuration according to example embodiments.

Referring further to FIGS. 1-5, obturator assembly 10 includes an obturator 40 movably positioned within lumen 30. Obturator 40 is movable between a first position, such as a closed position shown in FIG. 1, and a second position, such as an open position as shown in FIG. 3. Obturator 40 has a distal end 42 and an opposing proximal end 44. In certain embodiments, obturator 40 includes a tip portion 46 at distal end 42. Tip portion 46 transitions into a body 48 in a midsection of obturator 40 and body 48 transitions into a base 50 at proximal end 44 of obturator 40. In certain example embodiments as shown in FIGS. 6-8, body 48 and/or base 50 forms or defines a channel 52 providing fluid communication between lumen 30 and central passage 14. In example embodiments, with obturator 40 in the first position, distal end 42 and, in certain embodiments, tip portion 46, prevents or limits fluid communication and fluid flow through lumen 30. With obturator 40 in the second position, distal end 42 and, in certain embodiments, tip portion 46, provides fluid communication such that fluid is able to flow through lumen 30 into central passage 14 through channel 52. In particular embodiments, obturator 40 is made of a suitable translucent material to act as a conduit for light-based disinfectant technology used in reducing bioburden in the intraluminal space, for example.

In example embodiments, with obturator 40 in the first position, distal end 42, e.g., at least a portion of tip portion 46, is positioned within lumen 30 to prevent fluid flow into lumen 30 and, with obturator 40 in the second position, distal end 42, e.g., at least a portion of tip portion 46, extends from catheter 22 in a distal direction to allow fluid flow into lumen 30. Alternatively, in certain embodiments, with obturator 40 in the second position, distal end 42, e.g., at least a portion of tip portion 46, extends into lumen 30 of catheter 22 in a proximal direction to allow fluid flow into lumen 30. In example embodiments described herein, obturator 40 is movable from the first position to the second position in a distal direction with respect to distal end 24 of catheter 22, i.e., away from hub 12, to extend beyond distal end 24 to provide a fluid flow path 54 as shown, for example, in FIGS. 4 and 5. Fluid flow path 54 provides fluid communication between lumen 30 and a lumen formed in a vessel, e.g., an artery or vein of a patient in which obturator assembly 10 is positioned. Referring to FIGS. 1-5, in example embodiments, obturator 40 may be used independently of the other components of obturator assembly 10 and/or catheter 22 or may be used with any suitable combination of one or more components of obturator assembly 10 and/or catheter 22.

Referring again to FIGS. 6-8, in example embodiments, a fluid flow in obturator assembly 10, e.g., through at least lumen 30, is selectably controllable. For example, in certain example embodiments, obturator 40 is urged at proximal end 44, e.g., by pushing at base 50 and/or hub 12, to move obturator 40 in a first direction within lumen 30 in the distal direction with respect to distal end 24 of catheter 22 until distal end 42, e.g., at least a portion of tip portion 46, extends distally from lumen 30 of catheter 22 to provide fluid flow path 54 through lumen 30, as shown in FIGS. 7 and 8. Conversely, in these embodiments obturator 40 is urged at proximal end 44, e.g., by pulling at base 50 and/or hub 12, to move obturator 40 in a second direction opposite the first direction within lumen 30 until distal end 42, e.g., at least a portion of tip portion 46 is at least partially positioned within lumen 30 to close fluid flow path 54, as shown in FIG. 6. In certain embodiments, obturator 40 can be moved automatically in the distal direction and the proximal direction using a pump or another suitable device. In alternative example embodiments, obturator 40 is moveable in a proximal direction with respect to distal end 24 of catheter 22, i.e., toward hub 12, from the first position to the second position to extend into lumen 30 a suitable distance to provide a fluid flow path (not shown in the figures). The fluid flow path provides fluid communication between lumen 30 and the lumen formed in the patient's vessel.

Obturator assembly 10 includes one or more seals, such as one or more sleeve seals, formed plastic seals, O-ring seals, or any suitable seals known to those having ordinary skill in the art. In certain embodiments, one or more O-ring seals 56 or other suitable seals or gaskets, are positioned about an outer periphery 58 of proximal end 44 of obturator 40 and contact an inner surface 60 of small-bore connector 28 at proximal end 26 of catheter 22. In certain embodiments, each O-ring seal 56 is positioned within a respective annular slot 62 formed in inner surface 60 of small-bore connector 28 to properly maintain O-ring seal 56 positioned about proximal end 44 of obturator 40 and between obturator 40 and catheter 22 to provide a fluid-tight seal within obturator assembly 10.

Figure 4:
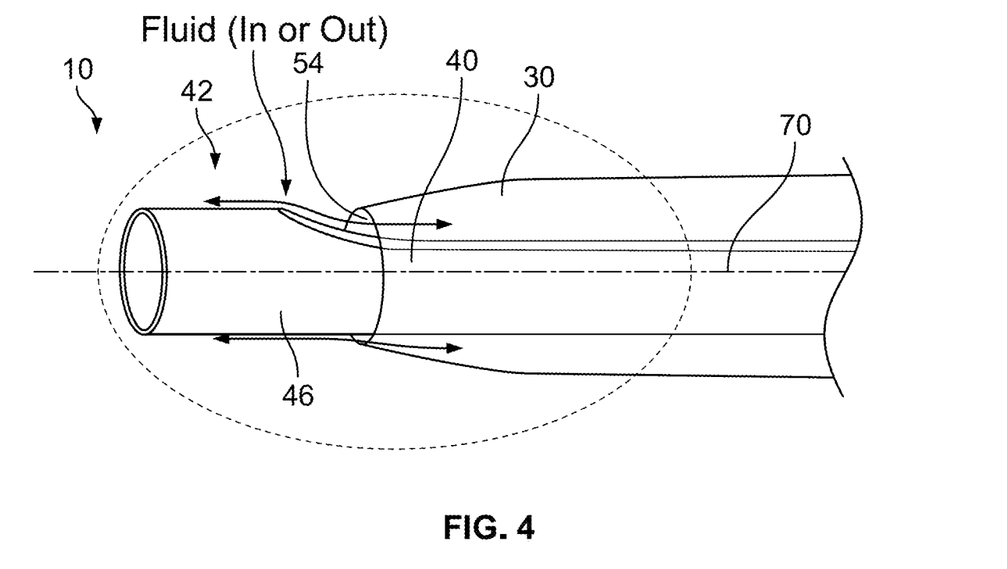
FIG. 4 is a partial perspective side view of the example obturator assembly shown in FIG. 3.
Figure 5:
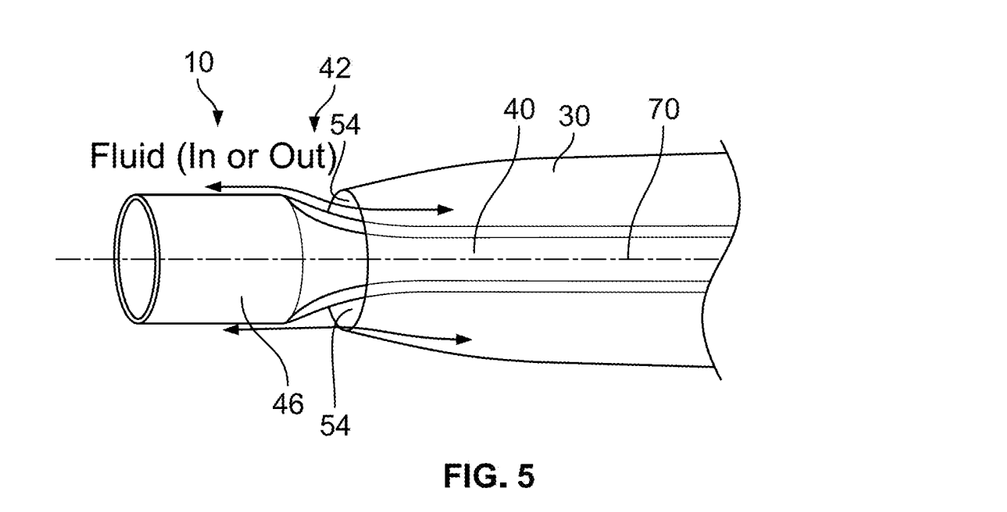
FIG. 5 is a partial perspective side view of the example obturator assembly shown in FIG. 3 with an alternative example obturator distal end.

Obturator 40 has a central axis 70, shown in FIGS. 2, 4, and 5, extending between distal end 42 and proximal end 44 of obturator 40. In example embodiments, at least a portion of distal end 42, e.g., at least a portion of tip portion 46, has an asymmetrical profile, such as shown in FIGS. 2 and 4, with respect to central axis 70 or a symmetrical profile, as shown in FIG. 5, with respect to central axis 70. Distal end 42, e.g., at least a portion of tip portion 46, may have any suitable profile that provides the desired fluid flow through fluid flow path 54. In certain conventional obturator assemblies, as a patient's blood is drawn past the distal end of an obturator and into a lumen of the cooperating catheter, shear forces exerted on the red blood cells may damage the red blood cells and may tear or rupture the red blood cells causing destruction and disassociation of the red blood cells, sometimes referred to as "hemolysis." Unlike distal ends of conventional obturators, distal end 42 and, particularly, at least a portion of tip portion 46, has a smooth, transitioning profile that facilitates administering or drawing fluids, e.g., blood, to or from the patient while preventing or limiting the damage and destruction of fluid material and the occurrence of hemolysis, for example.

In example embodiments, an amount of fluid flow (i.e., a volume of fluid) through fluid flow path 54 can be optimized by adjusting a cross-sectional area of an opening formed between an outer surface of obturator 40 and an inner wall of catheter 22 forming lumen 30. For example, an outer diameter of obturator 40 and/or an inner diameter of catheter 22 at the distal end of catheter 22 may be adjusted to reduce hemolysis and provide a desired blood sample during a blood draw application. For example, referring to FIG. 4, a relatively larger fluid flow path 54 may reduce or eliminate damage to the blood cells during the blood draw. Conversely, an equal amount of fluid flow through a smaller cross-sectional area, such as shown in FIG. 5, may provide better infusion performance because the flow is equally divided around the distal end of obturator 40.

As shown in FIGS. 1, 3, and 6-8, in example embodiments, obturator assembly 10 includes a collar, such as a locking collar 72, operatively coupled to hub 12. Locking collar 72 is configurable in a locked configuration, such as shown in FIGS. 6 and 8, to prevent movement of obturator 40 within lumen 30 and in an unlocked configuration, such as shown in FIG. 7, to allow movement of obturator 40 in the distal direction and/or the opposite proximal direction within lumen 30. In the locked configuration, locking collar 72 is configured to retain obturator 40 in a selected position, e.g., the first position or the second position. In FIG. 6, locking collar 72 is in the locked configuration to retain obturator 40 in the first position, e.g., a closed position preventing fluid flow through lumen 30, and prevent obturator from moving from the first position, e.g., to the second position. In FIG. 7, locking collar 72 is in the unlocked configuration to allow obturator 40 to move with respect to catheter 22 in a distal direction or an opposite proximal direction. As shown in FIG. 7, with locking collar 72 in the unlocked configuration, obturator 40 can be moved to the second position, e.g., an open position creating fluid flow path 54 to allow fluid flow into lumen 30. In FIG. 8, with locking collar 72 in the locked configuration, obturator 40 is retained in the second position, e.g., the open position creating fluid flow path 54, and prevented from moving from the second position, e.g., to the first position.

In certain embodiments, locking collar 72 includes a tab 74 positionable within or configured to interfere with a depression 76 formed in obturator 40 with locking collar 72 in the locked configuration. Tab 74 is actuatable to allow locking collar 72 to move between the locked configuration and the unlocked configuration. For example, in example embodiments, tab 74 is depressed to allow locking collar 72 to move from the locked configuration to the unlocked configuration, which allows obturator 40 to move between the first position and the second position. In certain example embodiments, locking collar 72 is biased toward the locked configuration in one of the first position and the second position. More specifically, tab 74 may be biased, using a spring or other suitable biasing member (not shown in the figures), toward the locked configuration in one of the first position and the second position.

Figure 9:
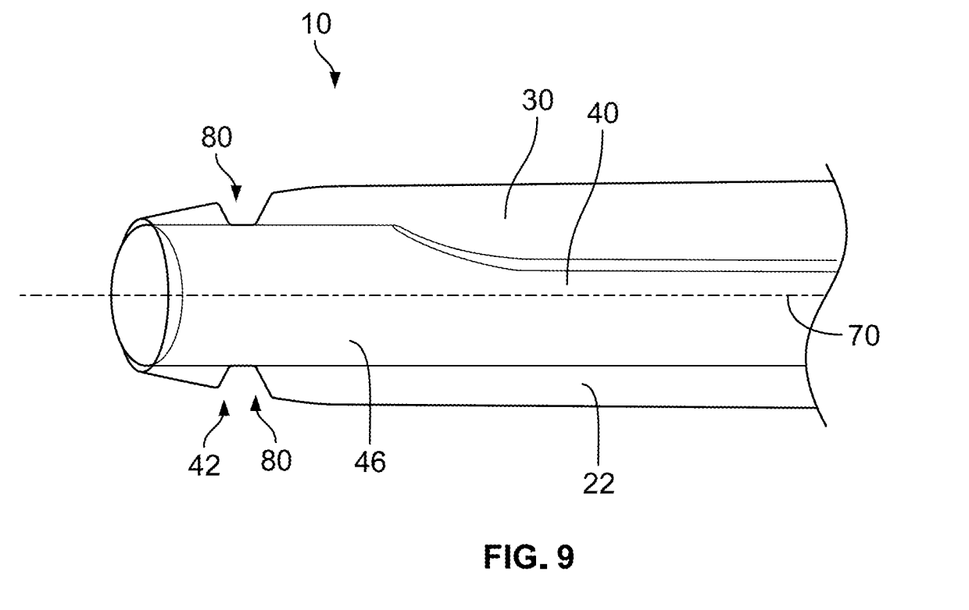
FIG. 9 is a partial perspective side view of an alternative example obturator assembly with an example obturator distal end.
Figure 10:
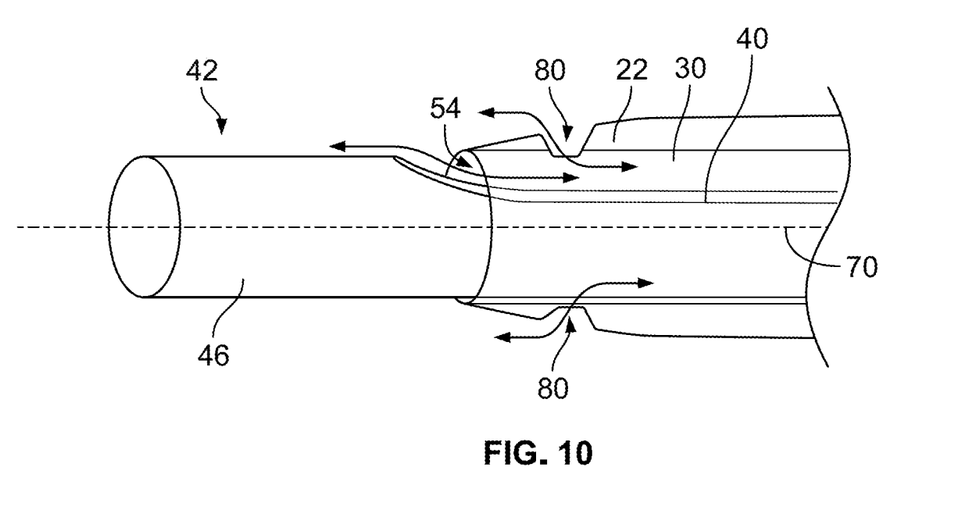
FIG. 10 is a perspective side view of the example obturator assembly of FIG. 9 in an open fluid flow path configuration according to example embodiments.
Figure 11:
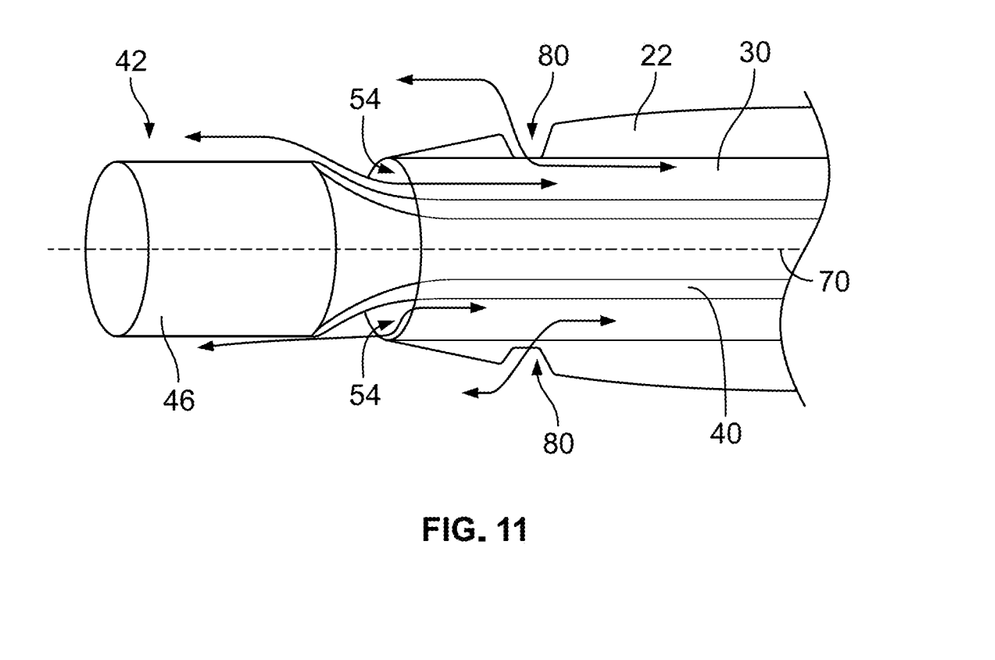
FIG. 11 is a partial perspective side view of an alternative example obturator assembly with an alternative example obturator distal end in a fully open fluid flow path configuration according to example embodiments.
Figure 12:
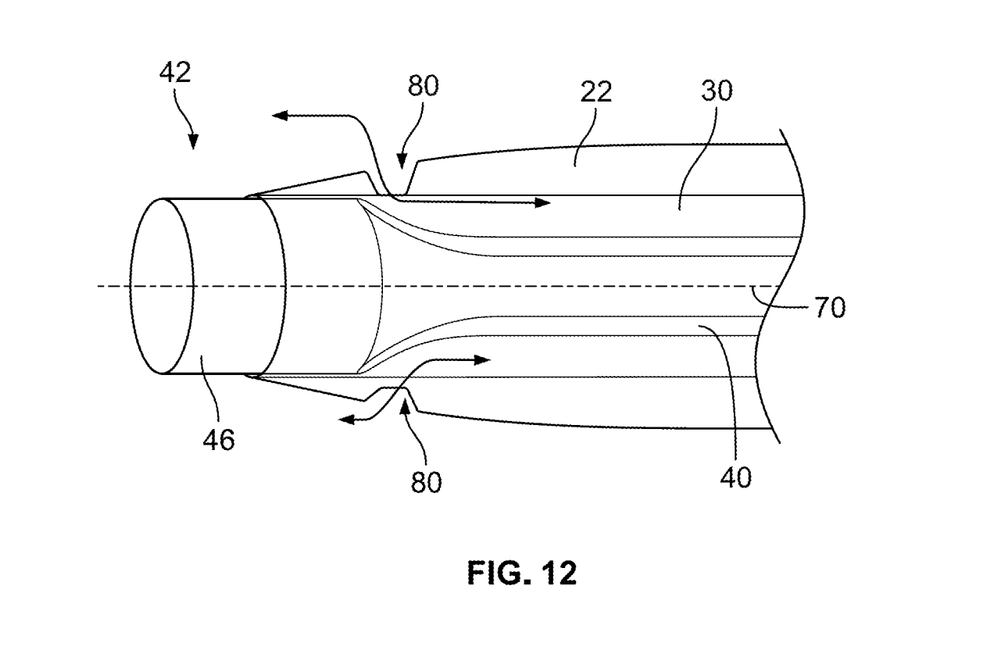
FIG. 12 is a perspective side view of the example obturator assembly of FIG. 11 in a partially open fluid flow path configuration according to example embodiments.

Referring to FIGS. 9-12, in alternative example embodiments, one or more diffuser openings 80 are formed through catheter 22 to provide fluid communication between lumen 30 and a lumen formed in a vessel, e.g., an artery or vein of a patient in which obturator assembly 10 is positioned. In these embodiments, at least a portion of distal end 42, e.g., at least a portion of tip portion 46, has an asymmetrical profile, such as shown in FIGS. 9 and 10, with respect to central axis 70 or a symmetrical profile, as shown in FIGS. 11 and 12, with respect to central axis 70. Distal end 42, e.g., at least a portion of tip portion 46, has a suitable length along central axis 70 such that, with obturator 40 in the closed position, distal end 42 extends into lumen 30 to seal the distal opening to lumen 30 as well as seal each diffuser opening 80 formed in catheter 22 to prevent or limit fluid flow through lumen 30, as shown in FIG. 9. As shown in FIGS. 10 and 11, with obturator 40 in a fully open position, fluid is allowed to flow through the distal opening of lumen 30 as well as through one or more diffuser openings 80. In a particular embodiment not shown in the figures, obturator 40 having an asymmetrical profile may seal one or more diffuser openings 80 preventing fluid flow through the sealed diffuser openings 80 while allowing fluid flow through diffuser openings nearest the asymmetrical aspect of obturator 40. Depending on the application of obturator assembly 10, fluid is allowed to flow into (e.g., fluid infusion) and/or out of (e.g., aspiration of fluid/blood drawn) lumen 30 through the distal opening of lumen 30 and diffuser openings 80. However, as shown in FIG. 12, with obturator 40 in an intermediate or partially open position, distal end 42, e.g., at least a portion of tip portion 46, extends into lumen 30 to seal the distal opening to lumen 30 but provides fluid communication or allows fluid flow through diffuser openings 80 formed in catheter 22. Again, depending on the application of obturator assembly 10, fluid is allowed to flow into and/or out of lumen 30 through diffuser openings 80 with the obturator in the partially open position. In these alternative embodiments, obturator 40 is configured to occlude diffuser holes 80 as well as the distal opening of lumen 30. This provides an added benefit of preventing occlusion at distal end 24 of catheter 22 and in or around diffuser openings 80. Diffuser openings 80 also provide an added benefit for blood draws by providing additional aspiration through diffuser openings 80 to further reduce hemolysis and may also be utilized for high-pressure injection.

Figure 13:
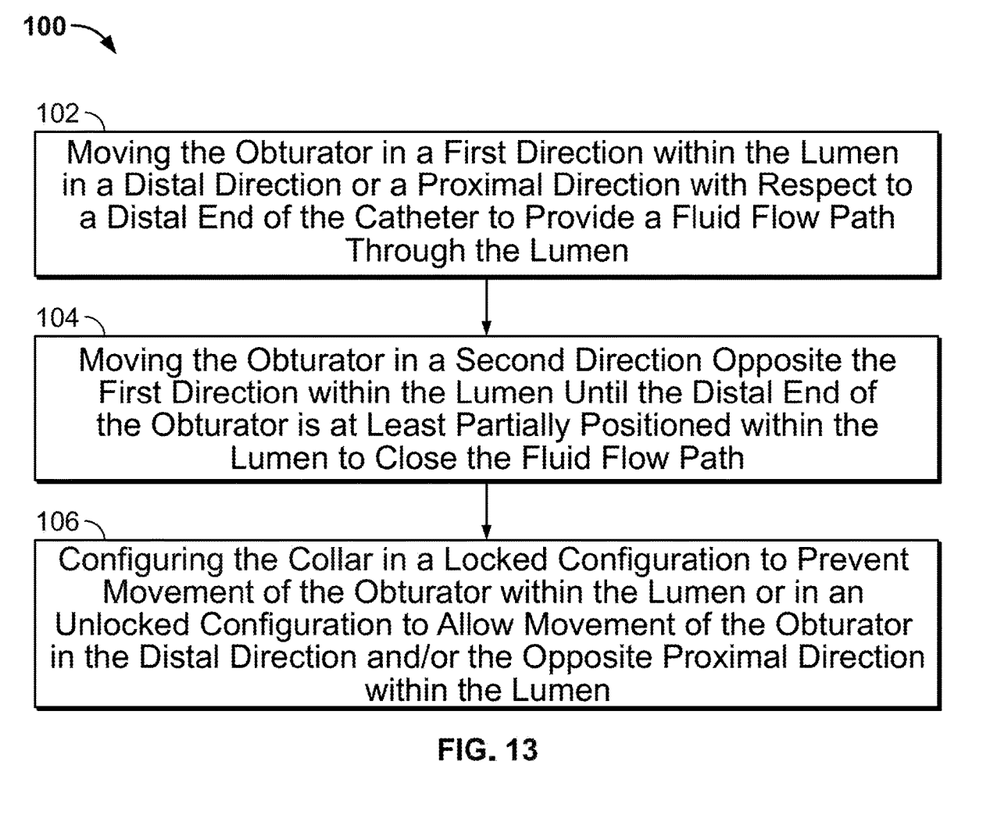
FIG. 13 illustrates steps of an example method for operating an example obturator assembly according to example embodiments.

FIG. 13 illustrates an example method 100 for selectively controlling a fluid flow in an obturator assembly. In example embodiments, the obturator assembly includes a catheter forming a lumen and an obturator positioned within the lumen and movable between a first position and a second position. The method includes moving 102 the obturator in a first direction within the lumen in one of a distal direction and a proximal direction with respect to a distal end of the catheter to provide a fluid flow path through the lumen. Moving 102 may include urging a proximal end of the obturator to move the obturator in a first direction within the lumen in a distal direction with respect to a distal end of the catheter, for example, to provide a fluid flow path through the lumen. As desired, the method also includes moving 104 the obturator in a second direction opposite the first direction within the lumen until the distal end, e.g., at least a portion of the tip portion, of the obturator is at least partially positioned within the lumen to close the fluid flow path. Moving 104 may include urging the proximal end of the obturator to move the obturator in a second direction opposite the first direction within the lumen until the distal end, e.g., at least a portion of the tip portion, of the obturator is at least partially positioned within the lumen to close the fluid flow path.

A collar, such as a locking collar, is operatively coupled to the hub of the obturator assembly. In example embodiments, the method includes configuring 106 the collar in a locked configuration to prevent movement of the obturator within the lumen or in an unlocked configuration to allow movement of the obturator in the distal direction and/or the opposite proximal direction within the lumen. In the locked configuration, the collar is configured to retain the obturator in a selected position, e.g., the first position or the second position. For example, the collar can be positioned in the locked configuration to retain the obturator in the first position, e.g., a closed position preventing fluid flow through the lumen, and prevent the obturator from moving from the first position, e.g., to the second position. The collar can also be positioned in the locked configuration to retain the obturator in the second position, e.g., the open position creating a fluid flow path, and prevent the obturator from moving from the second position, e.g., to the first position. The collar can also be positioned in the unlocked configuration to allow the obturator to move with respect to the catheter in a distal direction or an opposite proximal direction. With the collar in the unlocked configuration, the obturator can be moved between the first position and the second position, for example. In certain example embodiments, the collar is biased toward the locked configuration in one of the first position and the second position. More specifically, a tab of the collar may be biased, using a spring or other suitable biasing member, toward the locked configuration in one of the first position and the second position.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. An obturator assembly, comprising:
   a hub forming a central passage;
   a catheter having a distal end and an opposing proximal end, the catheter including a small-bore connector at the proximal end coupled to the hub, the catheter forming a lumen extending between the distal end and the proximal end of the catheter, the lumen in fluid communication with the central passage;
   an obturator movably positioned within the lumen, the obturator movable between a first position and a second position, the obturator including a distal end having a tip portion, wherein, with the obturator in the first position, the distal end of the obturator limits fluid flow through the lumen and, with the obturator in the second position, the distal end of the obturator provides a fluid flow path through the lumen; and
   a locking collar operatively coupled to the hub, the locking collar configurable in a locked configuration to prevent movement of the obturator within the lumen and in an unlocked configuration to allow movement of the obturator within the lumen, wherein, in the locked configuration, the locking collar is configured to prevent movement of the obturator within the lumen with the obturator in the first position or the second position, wherein the locking collar comprises a tab configured to selectively interfere with a depression formed in the obturator with the locking collar in the locked configuration.

2. The obturator assembly of claim 1, wherein the obturator is movable in one of a distal direction with respect to the distal end of the catheter or a proximal direction with respect to the distal end of the catheter from the first position to the second position.

3. The obturator assembly of claim 1, wherein the locking collar is biased toward the locked configuration with the obturator in one of the first position or the second position.

4. The obturator assembly of claim 1, wherein the obturator has a central axis extending between the distal end and a proximal end of the obturator, at least a portion of the distal end having one of a symmetrical profile with respect to the central axis or an asymmetrical profile with respect to the central axis.

5. The obturator assembly of claim 1, wherein the hub comprises a small-bore connector configured to couple the hub to a tube.

6. The obturator assembly of claim 1, wherein, with the obturator in the first position, the tip portion is positioned within the lumen to prevent fluid flow into the lumen and, with the obturator in the second position, the tip portion extends from the catheter in a distal direction to allow fluid flow into the lumen.

7. The obturator assembly of claim 1, wherein, with the obturator in the first position, the tip portion is positioned within the lumen to prevent fluid flow into the lumen and, with the obturator in the second position, the tip portion extends into the lumen of the catheter in a proximal direction to allow fluid flow into the lumen.

8. The obturator assembly of claim 1, wherein a proximal end of the obturator forms a channel in fluid communication with the lumen, the obturator assembly further comprising a seal positioned about an outer periphery of the proximal end of the obturator and contacting an inner surface of the small-bore connector at the proximal end of the catheter.

9. The obturator assembly of claim 8, wherein the seal comprises an O-ring seal positioned within an annular slot formed in the inner surface of the small-bore connector.

10. The obturator assembly of claim 1, wherein the tab is configured to selectively interfere with the depression in response to the obturator being in the first position, wherein the tab is configured to selectively interfere with another depression formed in the obturator in response to the obturator being in the second position.

11. An obturator assembly, comprising:
    an obturator movably positioned within a lumen of a device, the obturator movable between a first position and a second position, the obturator comprising a distal tip portion, wherein, with the obturator in the first position, the distal tip portion limits fluid communication through the lumen and, with the obturator in the second position, the distal tip portion provides fluid communication through the lumen; and
    a locking collar configurable in a locked configuration to prevent movement of the obturator within the lumen and in an unlocked configuration to allow movement of the obturator within the lumen, wherein, in the locked configuration, the locking collar is configured to prevent movement of the obturator within the lumen with the obturator in the first position or the second position, wherein the locking collar comprises a tab configured to selectively interfere with a depression formed in the obturator with the locking collar in the locked configuration.

12. The obturator assembly of claim 11, wherein the obturator is movable in at least one of a distal direction with respect to a distal end of the device or a proximal direction with respect to the distal end of the device from the first position to the second position.

13. The obturator assembly of claim 11, further comprising:
   a hub forming a central passage in fluid communication with the lumen.

14. The obturator assembly of claim 11, wherein the collar is biased toward the locked configuration with the obturator in one of the first position or the second position.

15. The obturator assembly of claim 11, wherein the obturator has a central axis extending between the distal end and the proximal end of the obturator, at least a portion of the distal end having one of a symmetrical profile with respect to the central axis or an asymmetrical profile with respect to the central axis.

16. The obturator assembly of claim 11, wherein the obturator is configured to move automatically in a distal direction toward the second position in response to a pressure causing fluid to flow through the lumen in the distal direction to allow the fluid to be expressed from the lumen.

17. The obturator assembly of claim 16, wherein, with the pressure removed, the obturator is configured to move automatically toward the first position.

\* \* \* \* \*